United States Patent [19]

Schow et al.

[11] Patent Number: 5,290,566
[45] Date of Patent: Mar. 1, 1994

[54] TOOTH WHITENING FORMULATION AND METHOD

[76] Inventors: Robert S. Schow, 2227 Highgate Rd., West Lake, Calif. 91631; Robert M. Drosman, 4767 Nomad, Woodland Hills, Calif. 91364

[21] Appl. No.: 629,146

[22] Filed: Dec. 18, 1990

[51] Int. Cl.$^5$ .................... A61K 33/40; A61K 9/10; A61K 47/38; A61K 6/00
[52] U.S. Cl. ..................... 424/488; 424/49; 424/53; 424/54
[58] Field of Search ............ 424/49, 54, 488, 53

[56] References Cited

U.S. PATENT DOCUMENTS

| | | | |
|---|---|---|---|
| 4,983,379 | 1/1991 | Schaeffer | 424/53 |
| 4,988,500 | 1/1991 | Hunter et al. | 424/81 |
| 4,990,089 | 2/1991 | Munro | 433/215 |
| 5,008,106 | 4/1991 | Meriands et al. | 424/53 |
| 5,009,885 | 4/1991 | Yarborough | 424/53 |

OTHER PUBLICATIONS

Bowles W., Thompson L., "Vital Bleaching: The Effects of Heat and Hydrogen Peroxide on Pulpal Enzymes", *Journal of Endodontics*, 12 No. 3: 108-122 (1986).

Epstein S., "Clinical Comparison ...", *Oral Surgery*, 32 No. 6:886-890 (1971).

Feinman R. A., Goldstein R. E., Garber D. A., "Bleaching Teeth", *Quintessence*, Chicago Publishing Co., Inc. (1987).

McCloskey R. J., "A Technique for Removal of Fluorosis Stains", *Journal of American Dental Association*, 109:63-64 (1984).

Baumgartner J., Reid D., Pickett A., "Human Pulpal Reaction to the Modified McInnes Bleaching Technique", *Journal of Endodontics*, 9:527-9 (1983).

Titley K., Torneck C., Smith D., "Effects of Concentrated Hydrogen Peroxide Solutions on the Surface Morphology of Human Tooth Enamel", *Journal of Endodontics*, 14, No. 2:69-74 (1988).

Bowles W., "Pulp Chamber Pentration by Hydrogen Peroxide Following Vital Bleaching", *Journal of Endodontics*, 12, No. 8:375-377 (1987).

Haywood et al, Nightguard Vital Bleaching, Quintessence International 20; 1989; pp. 173-176.

*Primary Examiner*—Edward Webman
*Attorney, Agent, or Firm*—Bryan Cave

[57] ABSTRACT

A tooth whitening formulation comprising urea peroxide (1:1) in a concentration of 22-32% based on the total weight of the formulation, in combination with a gelling agent, is provided in accordance with the present invention. The invention also provides a method for whitening the teeth using said formulation wherein the formulation is applied to the teeth using a splint which keeps the formulation in contact with the teeth for a period of time sufficient to cause whitening thereof.

6 Claims, No Drawings

TOOTH WHITENING FORMULATION AND METHOD

FIELD OF THE INVENTION

The invention relates to a tooth whitening formulation employing urea peroxide as active ingredient in a gel formulation. The invention also relates to a method of using said tooth whitening formulation.

BACKGROUND

There are several approaches available for bleaching and whitening teeth externally. Heat/catalyzed chemical procedures are well known. For example one technique involves vital bleaching of discolored or intrinsically stained teeth utilizing 37% phosphoric acid which etches the enamel, and then bleaching the teeth by applying 30% hydrogen peroxide to the tooth surface followed by heat application by a heating element. The time required will vary with tooth sensitivity. However, according to Bowles, et al., "Vital Bleaching: The Effects Of Heat And Hydrogen Peroxide On Pulpal Enzymes", Journal of Endodontics 12, 1084-112 (1986) both heat and hydrogen peroxide have been demonstrated to have deleterious effects on pulpal tissues.

Other techniques involve the superficial removal of enamel with abrasive instruments or pumice followed by treatment with additional caustic agents.

More recently, bleaching techniques suitable for home use have been developed. For example, Hayward, "Night Guard Vital Bleaching . . . ", Quintessence International 20, 173-177 (1989), describes a 10% carbamide (urea)/peroxide solution which is placed in a "Night Guard" and worn at night for several weeks to brighten teeth. According to Haywood, et al, no significant caustic chemical agents are used and only two short office visits are required to initiate treatment. This obviously provides a significant savings of cost and time for the patient.

SUMMARY OF THE INVENTION

It has now been found that a tooth whitening formulation employing between about 22-32% (w/w) urea/peroxide (1:1) as active ingredient in a gel formulation offers significant improvements over the tooth whitening procedures heretofore known. The tooth whitening formulation and method according to the present invention provides a more uniform lightening of the teeth from bicuspids to the incisors. Additionally, it has now been found that with the tooth whitening formulation and method according to the present invention it is possible to lighten teeth from the linguals when a plastic bonding has been put on the labial surfaces during previous treatments. It has been found that the gel formulation sits on the teeth and does not slip away. This permits the active ingredient to more uniformly penetrate the tooth to effect a more uniform lightening.

According to the present invention about 5 cc of the gel formulation is applied into a splint and inserted over the patients' teeth. Any material that extrudes out of the splint is wiped away with a tissue. The patients wear the splint for a minimum of six hours daily, generally during evening and sleep hours. The procedure is repeated on a daily basis until maximum whitening or lightening of the dentition occurs.

DETAILED DESCRIPTION OF THE INVENTION

The preparation of the tooth whitening formulation according to the invention will be set forth below. Unless otherwise indicated, all percentages are on a weight basis.

A 22% urea peroxide solution is prepared as follows. Urea peroxide (1:1), Spectrum Chemical Co., 14422 South San Pedro Street, Gardenia, Calif., 110 grams, is dissolved in 20 cc boiling water. Methylcellulose (400 CPS), 86 grams, is dissolved in 60 cc boiling water and triturated until a smooth texture is obtained. The dissolved urea peroxide solution is added to the methylcellulose and triturated until uniform. Next, sufficient water is added to bring the total mixture to 500 cc.

In similar manner, a 32% urea peroxide (1:1) solution is prepared following the foregoing procedure but, however, substituting 160 grams urea peroxide for the 110 grams used in the previous example.

The method of the invention will now be described as follows.

Impressions are taken on the maxillary and mandibular arch of a patient in need of tooth whitening to attain accurate models of the mouth. Initial photographs are taken with a static color from an existing shade guide used as a reference point.

A custom clear acrylic splint is fabricated over the models of the teeth that are the target to lighten. This clear splint is 0.02 inches thick and covers the lingual and labial tooth surfaces. The splint is fabricated in known manner using a Stavac ™ device, Buffalo Dental Co., 575 Underhill Boulevard, Syosset, N.Y. 11791.

This splint is placed onto the teeth to verify a good fit and no creation of occlusal disharmony.

Approximately 5 cc of the tooth whitener gel is applied into the splint and inserted over the teeth. Any material that extrudes out of the splint is wiped away with a tissue. Patients wear the splint at a minimum of six hours daily, generally in the evening and sleep hours. The tooth whitener is thus administered on a daily basis until maximum whitening or lightening of the dentition occurs.

Surprisingly, it has been found that the tooth whitening gel in accordance with the present invention is capable of bringing about more uniform lightening of the teeth from bicuspids to the incisors than has heretofore been possible and penetrates through the tooth so that it is possible to lighten teeth from the linguals when a plastic bonding has been put on the labial surfaces during previous treatments.

It is envisioned that urea/peroxide concentrations within the range of 22-32% may be used to make the tooth whitening gel according to the formulation. In addition, other gelling agents as are known in the art may be used in place of the methylcellulose.

It should be understood that the preferred embodiments and examples described are for illustrative purposes only and are not to be construed as limiting the scope of the present invention which is properly delineated only in the appended claims.

What is claimed is:

1. In a tooth whitener employing urea peroxide as the whitening agent, the improvement comprising:
   said tooth whitener being formulated as a gel comprising urea peroxide in a concentration of about 32% based on the total weight of the formulation, in combination with a gelling agent.

2. The tooth whitener formulation in accordance with claim 1, wherein the gelling agent is methylcellulose.

3. A method for whitening the teeth of a patient in need of tooth whitening, said method consisting essentially of applying as the tooth whitener a urea peroxide gel formulation wherein the urea peroxide is in a concentration of between about 22-32% based on the total weight of the formulation, to the teeth of a patient in need of whitening using a splint containing a tooth whitening effective amount of said tooth whitener and maintaining said tooth whitener in contact with the teeth for a time period sufficient to cause whitening thereof.

4. The method in accordance with claim 3, wherein the time period is at least six hours and wherein said method is repeated daily for a period sufficient to cause maximum whitening of the patient's teeth.

5. The method in accordance with claim 4, wherein the concentration is about 32%.

6. The method in accordance with claim 3, wherein the concentration is about 32%.

* * * * *

UNITED STATES PATENT AND TRADEMARK OFFICE
CERTIFICATE OF CORRECTION

PATENT NO. : 5,290,566

DATED : March 1, 1994

INVENTOR(S): ROBERT F. SCHOW ET AL.

It is certified that error appears in the above-identified patent and that said Letters Patent is hereby corrected as shown below:

Title page, item [76]
Change the name of the first named inventor from "Robert S. Schow" to --Robert F. Schow--.

Signed and Sealed this

Thirtieth Day of August, 1994

Attest:

BRUCE LEHMAN

*Attesting Officer*  *Commissioner of Patents and Trademarks*